US011837330B2

(12) United States Patent
Kinney (10) Patent No.: US 11,837,330 B2
(45) Date of Patent: *Dec. 5, 2023

(54) REFERENCE-GUIDED GENOME SEQUENCING

(71) Applicant: Western Digital Technologies, Inc., San Jose, CA (US)

(72) Inventor: Justin Kinney, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 932 days.

This patent is subject to a terminal disclaimer.

(21) Appl. No.: 16/822,010

(22) Filed: Mar. 18, 2020

(65) Prior Publication Data

US 2021/0295946 A1    Sep. 23, 2021

(51) Int. Cl.
| | | |
|---|---|---|
| G16B 30/10 | (2019.01) | |
| G16B 50/30 | (2019.01) | |
| G16B 30/20 | (2019.01) | |
| G06N 7/01 | (2023.01) | |
| G16B 5/20 | (2019.01) | |

(52) U.S. Cl.
CPC .............. *G16B 5/20* (2019.02); *G06N 7/01* (2023.01); *G16B 30/10* (2019.02); *G16B 50/30* (2019.02); *G16B 30/20* (2019.02)

(58) Field of Classification Search
None
See application file for complete search history.

(56) References Cited

U.S. PATENT DOCUMENTS

| | | |
|---|---|---|
| 8,634,247 B1 | 1/2014 | Sprouse et al. |
| 9,098,403 B2 | 8/2015 | Sprouse et al. |
| 9,600,625 B2 | 3/2017 | Asadi et al. |
| 9,639,501 B1 | 5/2017 | Gazit et al. |

(Continued)

FOREIGN PATENT DOCUMENTS

| | | |
|---|---|---|
| CA | 2854084 C | 11/2019 |
| CN | 101866357 A | 10/2010 |

(Continued)

OTHER PUBLICATIONS

Eloi Araujo, Marco A. Stefanes, Valter de O. Ferlete. Multiple Sequence Alignment using Hybrid Parallel Computing. 2017 IEEE 17th International Conference on Bioinformatics and Bioengineering (Year: 2017) (Year: 2017).*

(Continued)

*Primary Examiner* — Soren Harward
*Assistant Examiner* — Mary C Leverett
(74) *Attorney, Agent, or Firm* — Barry IP Law, P.C.

(57) ABSTRACT

Methods and systems for processing a plurality of sample reads for genome sequencing include, for each sample read of the plurality of sample reads, comparing substring sequences from the sample read to reference sequences representing different portions of a reference genome. One or more reference sequences are identified that match one or more of the compared substring sequences, and a probabilistic location within the reference genome is determined for the sample read based on the one or more identified reference sequences. The reference genome is partitioned for reference-aligned genome sequencing based on the determined probabilistic locations of the respective sample reads.

21 Claims, 6 Drawing Sheets

(56) References Cited

U.S. PATENT DOCUMENTS

| | | |
|---|---|---|
| 9,734,284 B2 | 8/2017 | Olson |
| 2010/0138376 A1 | 6/2010 | Avis et al. |
| 2013/0246698 A1 | 9/2013 | Estan et al. |
| 2014/0136120 A1 | 5/2014 | Colwell et al. |
| 2014/0172824 A1 | 6/2014 | Musuvathi et al. |
| 2014/0347933 A1 | 11/2014 | Lee |
| 2014/0371110 A1* | 12/2014 | Van Rooyen ..... H01L 21/76886 438/618 |
| 2017/0235876 A1 | 8/2017 | Jaffe et al. |
| 2017/0337325 A1 | 11/2017 | Olson |
| 2019/0214111 A1 | 7/2019 | Alberti et al. |
| 2021/0201163 A1 | 7/2021 | Kalsi et al. |

FOREIGN PATENT DOCUMENTS

| | | |
|---|---|---|
| EP | 2759952 A1 | 7/2014 |
| EP | 3673386 A1 | 7/2020 |

OTHER PUBLICATIONS

Benkrid, Khaled, Ying Liu, and AbdSamad Benkrid. "A highly parameterized and efficient FPGA-based skeleton for pairwise biological sequence alignment." IEEE Transactions on Very Large Scale Integration (VLSI) Systems 17.4 (2009): 561-570. (Year: 2009).*

Houtgast, Ernst Joachim, et al. "An FPGA-based systolic array to accelerate the BWA-MEM genomic mapping algorithm." 2015 international conference on embedded computer systems: Architectures, modeling, and simulation (samos). IEEE, 2015. (Year: 2015).*

Shah, Hurmat Ali, Laiq Hasan, and Insoo Koo. "Optimized and Portable FPGA-Based Systolic Cell Architecture for Smith? Waterman-Based DNA Sequence Alignment." Journal of information and communication convergence engineering 14.1 (2016): 26-34. (Year: 2016).*

Pending U.S. Appl. No. 16/820,711, filed Mar. 17, 2020, entitled "Devices and Methods for Locating a Sample Read in a Reference Genome", Justin Kinney.

Pending U.S. Appl. No. 16/821,849, filed Mar. 17, 2020, entitled "Reference-Guided Genome Sequencing", Justin Kinney.

Araujo et al.; "Multiple Sequence Alignment using Hybrid Parallel Computing"; 2017 IEEE 17th International conference on Bioinformatics and Bioengineering.

International Search Report and Written Opinion dated Oct. 22, 2020; International Application No. PCT/US2020/040568, 11 pages.

Pending U.S. Appl. No. 16/908,581, filed Jun. 22, 2020, entitled "Devices and Methods for Enome Sequencing", Wen Ma.

Houtgast, et al.; "An FPGA-Based Systolic Array to Accelerate the BWA-MEM Genomic Mapping Algorithm"; Delft University of Technology; Jul. 1, 2015; available at: http://pure.tudelft.nl/ws/files/10410158/3210798/pdf.

Huangfu, et al.; "RADAR: A 3D-ReRAM based DNA Alignment Accelerator Architecture"; Jun. 24, 2018; In Proceedings of the 55th Annual Design Automation Conference; https://seal.ece.ucsb.edu/sites/seal.ece.ucsb.edu/files/publications/a59-huangfu.pdf.

McVicar, et al.; "FPGA Acceleration of Short Read Alignment"; arXiv preprint arXiv:1805.00106; Apr. 30, 2018; available at: http://arxiv.org/ftp/arxiv/papers/1805/1805.00106.pdf.

Pfeiffer, et al.; "Hardware enhanced biosequence alignment"; International Conference on METMBS '05; vol. 5; Jun. 23, 2005; available at: http://citeseerx.ist.psu.edu/viewdoc/download?doi=10.1.1.85.5807&rep=rep1&type=pdf.

International Search Report and Written Opinion dated Oct. 11, 2020 from counterpart International Application No. PCT/US2020/040570, 18 pages.

Garro et al.; "Using a programmable network switch TCAM to find the best alignment of two DNA sequences"; Nov. 1, 2016; IEEE 36th Central American and Panama Convention (Concapan XXXVI); available at: https://ieeexplore.ieee.org/document/7942372.

Khatamifard et al.; "Read Mapping Near Non-Volatile Memory"; arXiv:1709.02381; May 5, 2020; available at: https://arxiv.org/abs/1709.02381.

Parag K Lala; "A CAM (Content Addressable Memory) Architecture for Codon Matching in DNA Sequences"; Current Journal of Applied Science and Technology; Jul. 10, 2015; available at https://www.journalcjast.com/index.php/CJAST/article/view/8357.

International Search Report and Written Opinion dated Jun. 16, 2021 from International Application No. PCT/US2021/014952, 9 pages.

Kaplan et al.; "A Resistive CAM Processing-in-Storage Architecture for DNA Sequence Alignment"; Jan. 17, 2017; 9 pages; available at: https://webee.technion.ac.il/people/ran/papers/ReCAMinStorageDNAsequenceIEEEmicro2017.pdf.

Kaplan et al.; "BioSEAL: In-Memory Biological Sequence Alignment Accelerator for Large-Scale Genomic Data"; Jan. 17, 2019; 14 pages; available at: https://arxiv.org/ftp/arxiv/papers/1901/1901.05959.pdf.

Li et al.; "NVSim-CAM: A Circuit-Level Simulator for EmergingNonvolatile Memory based Content-Addressable Memory"; 2017; 7 pages; available at: https://dl.acm.org/doi/pdf/10.1145/2966986.2967059.

Khatamifard et al.; "A Non-volatile Near-Memory Read Mapping Accelerator"; Mar. 23, 2018; 12 pages; available at: https://arxiv.org/pdf/1709.02381.pdf.

Amin, M. R., et al., "NanoBLASTer: Fast alignment and characterization of Oxford Nanopore single molecule sequencing reads", 2016 IEEE 6th International Conference on Computational Advances in Bio and Medical Sciences (ICCABS), pp. 1-6, (Oct. 13-15, 2016).

Ellis, M., et al., "diBELLA: Distributed Long Read to Long Read Alignment", arxiv.org, 48th International Conference on Parallel Processing (ICPP 2019), pp. 11, (Aug. 5-8, 2019).

Guidi, G., et al., "BELLA: Berkeley Efficient Long-Read to Long-Read Aligner and Overlapper", https://doi.org/10.1101/464420, pp. 30, (Oct. 10, 2019).

Chin et al.; "Nonhybrid, finished microbial genome assemblies from long-read SMRT sequencing data"; Nature.com; Nature Methods; May 5, 2013; p. 563-569; available at: https://www.nature.com/articles/nmeth.2474.

Houtgast et al.; "Hardware Acceleration of BWA-MEM Genomic Short Read Mapping for Longer Read Lengths"; Computational Biology and Chemistry; vol. 75; Aug. 2018; p. 54-64; available at https://doi.org/10.1016/j.compbiolchem.2018.03.024.

Liu et al.; "A Customized Many-Core Hardware Acceleration Platform for Short Read Mapping Problems Using Distributed Memory Interface with 3D-Stacked Architecture"; Journal of Signal Processing Systems; Dec. 3, 2016; p. 327-341; available at https://link.springer.com/article/10.1007/s11265-016-1204-8.

Xinyu Guo; "Design of A Systolic Array-Based FPGA Parallel Architecture for the BLAST Algorithm and Its Implementation"; The University of Toledo Digital Repository Theses and Dissertations; Aug. 2012available at: http://citeseerx.ist.psu.edu/viewdoc/download?doi=10.1.1.917.6897&rep=rep1&type=pdf.

Ye at al.; "DBG2OLC: Efficient Assembly of Large Genomes Using Long Erroneous Reads of the Third Generation Sequencing Technologies"; Nature.com; Scientific Reports; Aug. 30, 2016; 9 pages; available at: https://www.nature.com/articles/srep31900.

Lischer et al.; "Reference-guided de novo assembly approach improves genome reconstruction for related species"; BMC Bioinformatics; Nov. 10, 2017; 12 pages; available at https://bmcbioinformatics.biomedcentral.com/articles/10.1186/s12859-017-1911-6.

Hiatt et al.; "Parallel, tag-directed assembly of locally derived short sequence reads"; Nature.com; Nature Methods; Jan. 17, 2010; pp. 119-122; available at: https://www.nature.com/articles/nmeth.1416.

Gamaarachchi et al.; "Featherweight long read alignment using partitioned reference indexes"; Nature.com; Scientific Reports; Mar. 13, 2019; 12 pages; available at: https://www.nature.com/articles/s41598-019-40739-8.

Simpson et al.; "Efficient de novo assembly of large genomes using compressed data structures"; Genome Research; Dec. 7, 2011; 10 pages; available at: https://genome.cshlp.org/content/22/3/549.full?sid=896285ab-62e4-4258-9e15-5cef59a88f0c.

(56) References Cited

OTHER PUBLICATIONS

Huang et al.; "LW-FQZip 2: a parallelized reference-based compression of FASTQ files"; BMC Bioinformatics; Mar. 20, 2017; available at: https://bmcbioinformatics.biomedcentral.com/articles/10.1186/s12859-017-1588-x.

Janin et al.; "BEETL-fastq: a searchable compressed archive for DNA reads"; Bioinformatics; vol. 30; Issue 19, Oct. 2014; pp. 2796-2801; available at: https://academic.oup.com/bioinformatics/article/30/19/2796/2422232.

Hwang et al.; "Privacy-Preserving Compressed Reference-Oriented Alignment Map Using Decentralized Storage"; IEEE Access; Aug. 17, 2018; 12 pages; available at: https://ieeexplore.ieee.org/document/8438866.

Oenning et al.; "CompStor Novos: low cost yet fast assembly-based variant calling for personal genomes"; bioRxiv; Cold Spring Harbor Laboratory; Dec. 4, 2018; 16 pages; available at: https://www.biorxiv.org/content/10.1101/486092v1.

Canzar et al.; "Short Read Mapping: An Algorithmic Tour"; Mar. 2017; Proc IEEE Inst Electr Electron Eng.; 54 pages; available at: https://www.ncbi.nlm.nih.gov/pmc/articles/PMC5425171/pdf/nihms854488.pdf.

Jain et al.; "A fast adaptive algorithm for computing whole-genome homology maps"; Bioinformatics; 9 pages; Sep. 2018; available at: https://academic.oup.com/bioinformatics/article/34/17/1748/5093242.

Kim, et al.; "GRIM-Filter: Fast seed location filtering in DNA read mapping using processing-in-memory technologies"; BMC Genomics; vol. 19; Suppl. 2; May 9, 2018; 18 pages; available at: https://bmcgenomics.biomedcentral.com/articles/10.1186/s12864-018-4460-0.

Wilton et al.; "Faster sequence alignment through GPU-accelerated restriction of the seed-and-extend search space"; bioRxiv; Aug. 1, 2014; 7 pages; available at: https://www.biorxiv.org/content/10.1101/007641v1.full.

International Search Report and Written Opinion dated Oct. 27, 2020 from counterpart International Application No. PCT/US2020/040530, 10 pages.

Kento Aoyama, "Development of Exome Analysis Pipeline on the K Computer", Trans. IPS Japan, Advanced Computing Systems (ACS), vol. 9 No. 2 [online], Japan, IPS Japan, Jul. 14, 2016, vol. 9 No. 2, p. 15-33, ISSN:1882-7829.

Benkrid et al.; "A highly parameterized and efficient FPGA-based skeleton for pairwise biological sequence alignment"; IEEE Transactions on Very Large Scale Integration (VLSI) Systems 17.4 (2009): 561-570; Apr. 2009.

Shah et al; "Optimized and Portable FPGA-Based Systolic Cell Architecture for Smith-Waterman-Based DNA Sequence Alignment"; Journal of information and communication convergence engineering 14.1 (2016):26-34; Mar. 2016.

Lala et al.; "A CAM (Content Addressable Memory)-based architecture for molecular sequence matching"; Proceedings of the International Conference on Bioinformatics & Computational Biology (BIOCOMP), (Year: 2003).

Yu et al.; "A Smith-Waterman Systolic Cell"; Excerpt 13th International Conference, FPL 2003, Proceedings, p. 375-384 (Year: 2003).

Altschul et al.; "Basic Local Alignment Search Tool"; May 15, 1990; Journal of molecular biology; available at: https://pubmed.ncbi.nlm.nih.gov/2231712/.

Guo et al; "A systolic array-based FPGA parallel architecture for the BLAST algorithm"; International Scholarly Research Notices; 2012; available at https://www.ncbi.nlm.nih.gov/pmc/articles/PMC4417556/.

\* cited by examiner

FIG. 1

| $110_1$ | $110_2$ | $110_3$ | | $110_{L-19}$ |
|---|---|---|---|---|
| R1, S1 | R2, S1 | R3, S1 | | R(L-19), S1 |
| R2, S2 | R3, S2 | R4, S2 | | R(L-18), S2 |
| R3, S3 | R4, S3 | R5, S3 | | R(L-17), S3 |
| R4, S4 | R5, S4 | R6, S4 | | R(L-16), S4 |
| R5, S5 | R6, S5 | R7, S5 | | R(L-15), S5 |
| R6, S6 | R7, S6 | R8, S6 | | R(L-14), S6 |
| R7, S7 | R8, S7 | R9, S7 | | R(L-13), S7 |
| R8, S8 | R9, S8 | R10, S8 | | R(L-12), S8 |
| R9, S9 | R10, S9 | R11, S9 | | R(L-11), S9 |
| R10, S10 | R11, S10 | R12, S10 | ... | R(L-10), S10 |
| R11, S11 | R12, S11 | R13, S11 | | R(L-9), S11 |
| R12, S12 | R13, S12 | R14, S12 | | R(L-8), S12 |
| R13, S13 | R14, S13 | R15, S13 | | R(L-7), S13 |
| R14, S14 | R15, S14 | R16, S14 | | R(L-6), S14 |
| R15, S15 | R16, S15 | R17, S15 | | R(L-5), S15 |
| R16, S16 | R17, S16 | R18, S16 | | R(L-4), S16 |
| R17, S17 | R18, S17 | R19, S17 | | R(L-3), S17 |
| R18, S18 | R19, S18 | R20, S18 | | R(L-2), S18 |
| R19, S19 | R20, S19 | R21, S19 | | R(L-1), S19 |
| R20, S20 | R21, S20 | R22, S20 | | RL, S20 |

REFERENCE-GUIDED GENOME SEQUENCING

CROSS-REFERENCE TO RELATED APPLICATIONS

This application is related to co-pending application Ser. No. 16/820,711, filed on Mar. 17, 2020, and entitled "DEVICES AND METHODS FOR LOCATING A SAMPLE READ IN A REFERENCE GENOME", the entire contents of which are hereby incorporated by reference. This application is also related to co-pending application Ser. No. 16/821,849, filed on Mar. 17, 2020, and entitled "REFERENCE-GUIDED GENOME SEQUENCING", the entire contents of which are hereby incorporated by reference.

BACKGROUND

Limitations in current DNA (deoxyribonucleic acid) sample handling lead to sample reads or portions of a sample genome having a generally unknown location in the sample genome. For de novo sequencing, which does not use a reference genome in comparing sample reads to each other to locate the sample reads within the sample genome, the sample reads are typically analyzed as a single large group, which requires significant memory resources and a high computational cost to compare the sample reads in the large group to one another to determine locations for the sample reads within the sample genome. Such conventional methods of de novo sequencing are not scalable relative to the large amount of data that needs to be processed for genome sequencing. In more detail, conventional methods of de novo sequencing usually store a large group of sample reads in a shared memory, such as an expensive 2 TB DRAM. Since the number of compute cores that can connect to shared DRAM with independent high-bandwidth channels is limited (e.g., up to 24 cores), this arrangement limits the number of independent compute threads (e.g., up to 128 compute threads) that can be used for de novo sequencing.

For referenced-aligned sequencing, which uses a reference genome to locate sample reads within a sample genome, the full reference genome is typically searched for each sample read to locate the sample read within the reference genome. Such reference-aligned sequencing also requires significant memory resources to store the full reference genome and a high computational cost to compare each sample read to the full reference genome. Conventional methods of referenced-aligned sequencing also have limited scalability. In more detail, conventional methods of referenced-aligned sequencing may randomly partition the sample reads into groups that are processed by a corresponding compute thread. However, each compute thread typically needs a large dedicated memory, such as a 16 GB DRAM, to store the entire reference genome. In other techniques, the reference genome may be stored in a single shared 16 GB DRAM, but as noted above for conventional de novo sequencing, this shared memory arrangement limits the number of cores and compute threads that can access the shared memory. Accordingly, there is a need to improve genome sequencing in terms of computational cost, memory resources, and scalability.

BRIEF DESCRIPTION OF THE DRAWINGS

The features and advantages of the embodiments of the present disclosure will become more apparent from the detailed description set forth below when taken in conjunction with the drawings. The drawings and the associated descriptions are provided to illustrate embodiments of the disclosure and not to limit the scope of what is claimed.

DETAILED DESCRIPTION

In the following detailed description, numerous specific details are set forth to provide a full understanding of the present disclosure. It will be apparent, however, to one of ordinary skill in the art that the various embodiments disclosed may be practiced without some of these specific details. In other instances, well-known structures and techniques have not been shown in detail to avoid unnecessarily obscuring the various embodiments.

System Examples

Figure 1:
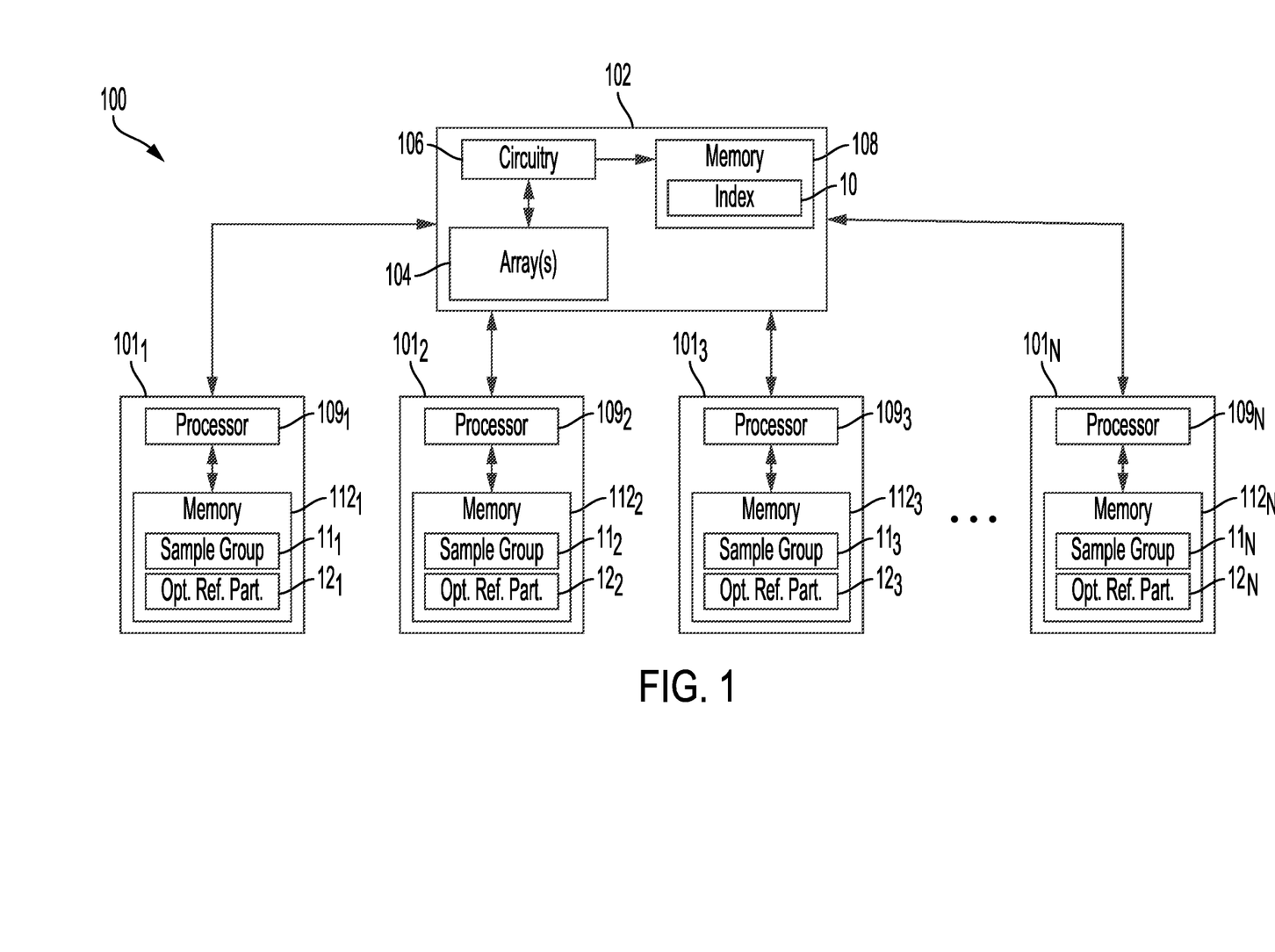
FIG. 1 is a block diagram of a system for genome sequencing according to one or more embodiments.

FIG. 1 is a block diagram of system 100 for genome sequencing including hosts $101_1$ to $101_N$ and reference-guided device 102 according to one or more embodiments. Hosts 101 communicate with reference-guided device 102 to receive respective sample groups $11_1$ to $11_N$ from reference-guided device 102 that include sample reads that have been sorted by reference-guided device 102. In other implementations, hosts 101 may instead receive an indication or data structure indicating which sample reads from a pool of sample reads to obtain from a shared memory for further processing by the respective host 101.

In implementations where hosts 101 perform reference-aligned sequencing, hosts 101 may also receive optional reference partitions $12_1$ to $12_N$, which include a portion of a reference genome, such as human reference genome H38, that corresponds to probabilistic locations determined for the sample reads. Optional reference partitions $12_1$ to $12_N$ may be received from device 102 or from another device, such as from a shared memory storing the full reference genome. As discussed in more detail below with reference to FIGS. 5 and 6, optional reference partitions $12_1$ to $12_N$ can be used by hosts 101 to align sample reads in the respective sample groups 11 into overlapping segments, or contigs, by comparing the sample reads in the sample group 11 to the associated reference partition 12.

In implementations where hosts 101 perform de novo sequencing, hosts 101 may not receive optional reference partitions $12_1$ to $12_N$. Hosts 101 in such de novo sequencing implementations align the sample reads in the respective sample groups 11 into overlapping segments, or contigs, by comparing the sample reads in the sample group 11 to other sample reads in the sample group.

For ease of description, the example embodiments in this disclosure will be described in the context of DNA sequencing. However, the embodiments of the present disclosure are not limited to DNA sequencing, and can be generally applied to any nucleic acid-based sequencing including RNA (ribonucleic acid) sequencing.

The sample reads in the example of FIG. 1 may initially be provided to reference-guided device 102 by one or more of hosts 101 or by another device not shown in FIG. 1 to determine probabilistic locations of the sample reads within a reference genome stored in one or more arrays 104 of device 102. In some implementations, a read device that generates the sample reads, such as an Illumina device (from Illumina, Inc. of San Diego, Calif.) or a nanopore device may provide sample reads to reference-guided device 102. In other implementations, one or more of hosts 101 or another device may provide reference-guided device 102 with sample substrings from the sample reads to determine probabilistic locations of the sample reads within the reference genome. For its part, device 102 may provide hosts 101 with index 10 stored in memory 108 of device 102 indicating probabilistic locations of the sample reads based on the sample substrings compared to the reference genome stored in one or more arrays 104 of device 102. Examples of device 102 and methods of probabilistically locating sample reads within a reference genome using device 102 are provided in related co-pending application Ser. No. 16/820,711, which is incorporated by reference above.

Hosts 101 can include, for example, a computer such as a desktop or server, smart storage devices, or other processing nodes, that may implement genome sequencing algorithms using processors 109, such as a seed and extend algorithm for exact matching and/or a more computationally complex algorithm, such as a Burrows-Wheeler algorithm or Smith-Waterman algorithm for approximate matching of sample reads in a genome. As discussed in more detail below, device 102 may be used to pre-process sample reads into sample groups 11 before de novo or referenced-aligned sequencing. In this regard, the probabilistic locations provided by reference-guided device 102 may replace or improve the efficiency of algorithms that would otherwise be performed by processors 109 of hosts 101 in terms of memory resources and computational cost. In addition, and as discussed in more detail below with reference to FIGS. 3 to 6, the probabilistic locations of sample reads provided by device 102 and sorting of the sample reads into sample groups 11 can allow for improvements to the scalability of genome sequencing, thereby lowering the expense and time to perform de novo or reference-aligned genome sequencing.

As shown in FIG. 1, each host 101 includes a processor 109 and a memory 112 storing a sample group 11 and optionally storing a reference partition 12. Processors 109 can include, for example, a Central Processing Unit (CPU), a Microprocessor (MPU), or a Microcontroller (MCU). Processor 109 may also be part of a System on a Chip (SoC).

Memories 112 of hosts 101 can include, for example, a volatile RAM such as DRAM, a non-volatile RAM, a Storage Class Memory (SCM), or other solid-state memory. A memory 112 can be accessed by a processor 109 to store and retrieve data used by the processor 109. In this regard, data stored in memory 112 can include instructions loaded from an application executed by processor 109, and/or data used in executing such applications.

While the description herein refers to solid-state memory generally, it is understood that solid-state memory may comprise one or more of various types of memory devices such as flash integrated circuits, Chalcogenide RAM (C-RAM), Phase Change Memory (PC-RAM or PRAM), Programmable Metallization Cell RAM (PMC-RAM or PMCm), Ovonic Unified Memory (OUM), Resistive RAM (RRAM), NAND memory (e.g., Single-Level Cell (SLC) memory, Multi-Level Cell (MLC) memory (i.e., two or more levels), or any combination thereof), NOR memory, EEPROM, Ferroelectric Memory (FeRAM), Magnetoresistive RAM (MRAM), other discrete Non-Volatile Memory (NVM) chips, or any combination thereof.

Reference-guided device 102 in some implementations can include, for example, one or more Application Specific Integrated Circuits (ASICs) or Field Programmable Gate Arrays (FPGAs) for generating index 10 indicating the probabilistic locations of sample substring sequences from a sample read relative to a reference genome. The probabilistic locations of the sample substring sequences can provide a host 101 or other device that stores a plurality of sample reads with a probabilistic location for the sample read from which the sample substring sequences were taken. As noted above, one or more of hosts 101 or another device in some implementations may provide reference-guided device 102 with a current sample substring sequence to load into the one or more arrays 104 of device 102. In other implementations, one or more of hosts 101 or another device may provide reference-guided device 102 with a sample read, and reference-guided device 102 may determine the sample substring sequences from the sample read to be loaded into the one or more arrays 104 for comparison with the reference genome.

Hosts 101 and device 102 may or may not be physically co-located. For example, in some implementations, hosts 101 and device 102 may communicate via a network, such as by using a Local Area Network (LAN) or Wide Area Network (WAN), such as the internet, or a data bus or fabric. In addition, those of ordinary skill in the art will appreciate that other implementations of system 100 may include multiple devices 102 for providing probabilistic locations of sample reads. In certain embodiments, one or more of hosts 101 and one or more devices 102 are integrated as a single device.

As shown in the example of FIG. 1, device 102 includes one or more arrays 104 of cells. As used herein, a cell generally refers to a memory location for storing one or more values representing one or more nucleotides, referred to as bases in the present disclosure. In some implementations, array or arrays 104 can include cells that also include logic for performing one or more operations on a value or values stored in the cell. In such examples, each cell in the one or more arrays can store a reference value representing a reference base from a reference genome and a sample value representing a base from a sample substring sequence. The cell may perform one or more operations to output a value that can be used by circuitry 106 or circuitry of the one or more arrays 104 to determine whether a group of cells in the one or more arrays 104 stores a reference sequence that matches the substring sequence stored in the group of cells. In some implementations, array(s) 104 can include one or more systolic arrays where a reference value representing a reference base from the reference genome is loaded, and a sample value representing a base from a sample substring sequence may be loaded into the cell for comparison to the reference value, before passing the sample value to a next cell in another group of cells of array(s) 104.

In other implementations, array or arrays 104 can include solid-state memory cells that may not perform operations to determine if the values stored in the cell match. For example, circuitry 106 in some implementations may determine if the values stored in each cell match. As another variation, array or arrays 104 may each store either a reference value representing a reference base or a sample value representing sample base. In such an implementation, cells storing reference values may be paired with cells storing sample values for comparison of the reference bases to the sample bases. In yet other implementations, the cells in array(s) 104 can include circuitry elements such as registers, latches, or flip-flops.

Circuitry 106 of device 102 can include, for example, hard-wired logic, analog circuitry and/or a combination thereof. In other implementations, circuitry 106 can include one or more ASICs, microcontrollers, Digital Signal Processors (DSPs), FPGAs, and/or a combination thereof. In some implementations, circuitry 106 can include one or more SoCs, which may be combined with memory 108. As discussed in more detail below, and as discussed in related application Ser. No. 16/820,711, circuitry 106 can be configured to identify groups of cells in array or arrays 104 where a stored reference sequence matches a current substring sequence stored in the group of cells.

In more detail, for each group of cells in array or arrays 104, a reference sequence for reference bases from a reference genome can be stored in the group of cells. The reference sequence corresponds to an order of the cells in the respective group of cells. Each group of cells is configured to store a reference sequence representing a portion of a reference genome that partially overlaps at least one other portion of the reference genome represented by one or more other reference sequences stored in one or more other groups of cells. An example of the storage of such overlapping reference sequences in an array is discussed in more detail below with reference to FIG. 2.

In addition, each group of cells in array or arrays 104 may be configured to store the same current substring sequence that corresponds to the order of the respective group of cells. As noted above, circuitry 106 is configured to identify groups of cells among the plurality of groups of cells in array or arrays 104 where the stored current substring sequence matches the reference sequence stored in the groups of cells. The identification of groups of cells with matching sequences may be made in some implementations by circuitry 106 based on values output from the cells after performing at least one logical operation, such as one or more XNOR operations and an AND operation. Although XNOR and AND are mentioned as examples, those or ordinary skill in the art will recognize that the same results can be achieved in other embodiments through different logic combinations. In other implementations, the identification of groups of cells with matching sequences may be made by circuitry 106 based on values output from the cells after multiplying a reference value representing the reference base and a sample value representing the sample base. In addition, circuitry 106 in some implementations may perform all of the operations on the values stored in the cells, instead of some of the operations being performed by the cells themselves.

Memory 108 of device 102 can include, for example, a volatile memory, such as DRAM, for storing index 10. In other implementations, memory 108 can include a nonvolatile memory, such as MRAM. As shown in FIG. 1, memory 108 stores index 10, which can be used to determine a probabilistic location of a sample read within the reference genome represented by the overlapping reference sequences loaded into or stored in array or arrays 104. In some implementations, index 10 can include a data structure, such as a bitmap or other data structure indicating an index or position in the reference genome corresponding to the groups of cells identified as storing matching sequences. Circuitry 106 may update index 10 for different sample substring sequences that are loaded into each group of cells of array(s) 104. In some implementations, circuitry 106 may indicate a mean location in index 10 for a substring sequence that has multiple matching groups of cells. In other implementations, only a first matching group of cells or certain matching groups of cells for a particular substring sequence may be used, or circuitry 106 may not update index 10 at all for a substring sequence that has more than a single group of cells storing matching sequences.

In addition, some implementations may not use an index or other data structure for indicating the location of groups of cells with matching sequences. For example, circuitry 106 in some implementations may output data directly to hosts 101 indicating groups of cells with matching sequences or may directly output sample reads that have been sorted into a particular sample group 11. In this regard, device 102 or another device in system 100 may perform the sorting of sample reads into groups 11 for hosts 101.

As will be appreciated by those of ordinary skill in the art with reference to the present disclosure, other implementations may include a different number or arrangement of components than shown for system 100 in the example of FIG. 1. For example, other implementations may combine device 102 with another device, such as a hardware accelerator (e.g., a Graphics Processing Unit (GPU)) configured to sort sample reads into sample groups 11, or may include a different number of devices 102, or include a dedicated device for sorting the sample reads into sample groups 11. As noted above, other implementations of system 100 may include a shared memory for temporarily storing the plurality of sample reads or portions of the plurality of sample reads before the sample reads are sorted into sample groups 11. In yet other implementations, device 102 may receive the sample reads as they are generated by a read device, such as an Illumina or nanopore device, that detects bases within a DNA sample.

Figure 2:
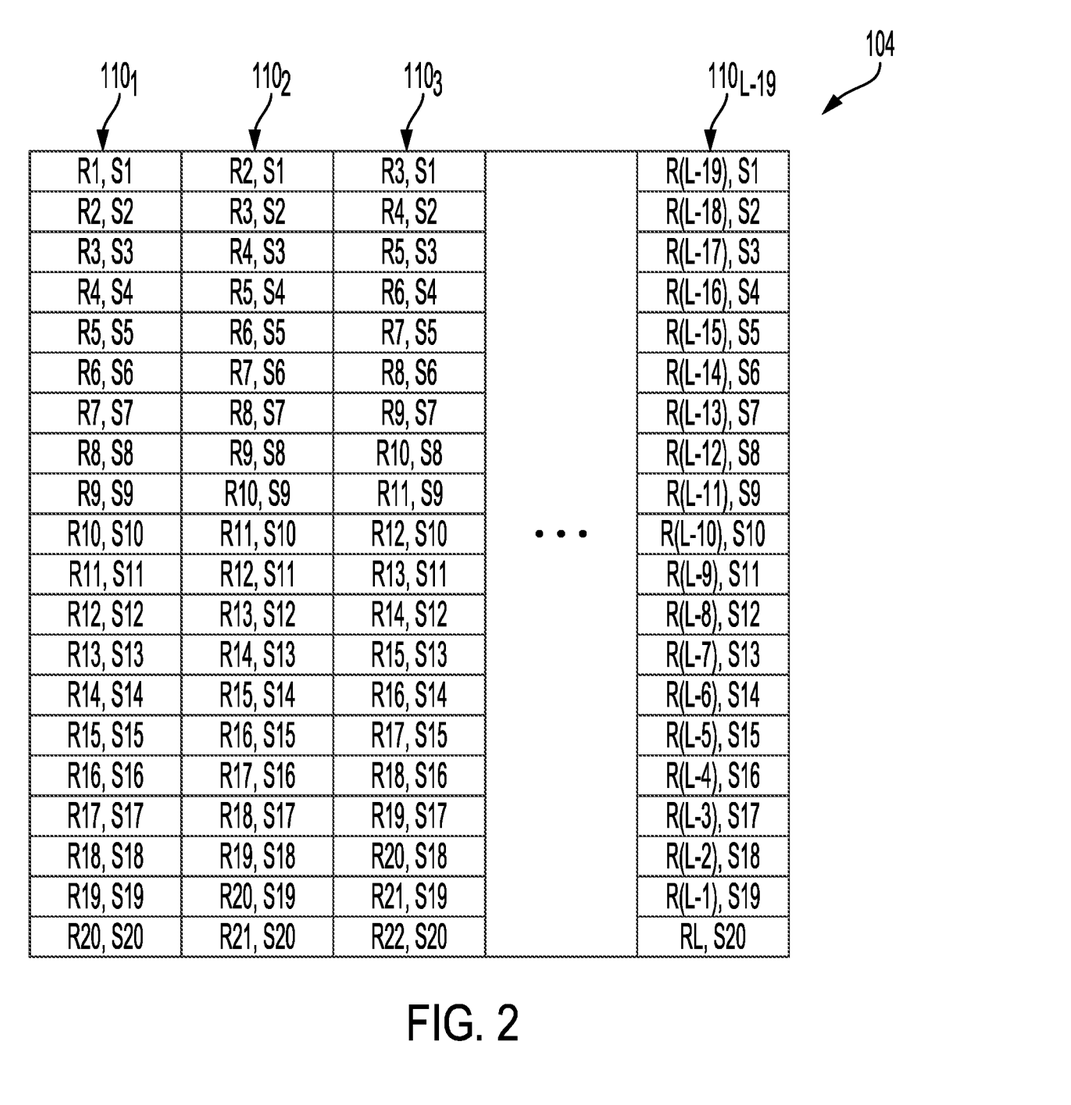
FIG. 2 illustrates an example of a plurality of groups of cells in a reference-guided device of the system of FIG. 1 according to one or more embodiments.

FIG. 2 illustrates an example of a plurality of groups of cells in reference-guided device 102 according to one or more embodiments. As shown in the example of FIG. 2, array 104 includes groups of cells 1101 to 110L-19. Although groups of cells 1101 to 110L-19 in FIG. 2 are shown as columns, other implementations may include groups of cells that are not physically arranged as columns. In some implementations, array 104 may substitute a defective cell from one group of cells with another cell located in a pool of spare cells in a different portion of the same array or in a different array. In implementations where each group of cells stores an overlapped reference sequence that has been shifted by one reference base from the previous group of cells, L can equal the full length of the reference genome, such as 3.2 billion groups or columns of cells, as in the case of the full reference human genome H38. Other implementations may instead store overlapped reference sequences that have been shifted by a different number of reference bases, such as by two reference bases, so that less groups of cells or columns are needed, which allows for a smaller size of array 104. However, shifting the overlap by more than one reference base can come at a cost of reducing the likelihood of finding matches for the substring sequence.

As shown in the example of FIG. 2, each group of cells 110 stores a reference value (e.g., R1, R2, R3, etc.) representing a reference base and a sample value (S1, S2, S3, etc.) representing a sample base. Each reference value and each sample value can be represented by two bits, since there are four possible bases—Adenine (A), Guanine (G), Cytosine (C), and Thymine (T), in the case of DNA sequencing, for example. While each group of cells 110 stores the same sample sequence of sample values S1 to S20, each group of cells 110 stores different partially overlapping reference sequences that are shifted by one reference base from a reference sequence stored in an adjacent group of cells. For example, group of cells 1101 stores a first reference sequence with reference values R1 to R20, and group of cells 1102 stores a second reference sequence with reference values R2 to R21. In other embodiments, the shifted-by offsets and resulting overlaps may be different across the cell groups than as shown in the example of FIG. 2.

The arrangement of storing partially overlapping reference sequences and substring sequences in array 104 ordinarily allows for an efficient locating of a probabilistic location of a sample read within the reference genome. In addition, the reference sequences only need to be loaded into or stored a single time in array 104. Iterations of loading or storing different substring sequences from a sample read may then provide a probabilistic location of the sample read within the reference genome, which may be used by host 101 to intelligently sort sample reads into groups of reads for more efficient de novo or reference-aligned sequencing, as discussed below with reference to the example processes of FIGS. 3 to 6. In this regard, different implementations may use a first type of cell, such as a ROM or NAND flash cell, to store the reference sequences, and a second type of cell that is better suited to repeated overwrites with a better write endurance, such as an MRAM cell, to store substring sequences.

A substring sequence length of 20 is used in the example of FIG. 2 including sample values S1 to S20. As discussed in more detail in related co-pending application Ser. No. 16/820,711, the length of the substring sequence, which corresponds to the number of cells in a group of cells or column, can be selected based on a desired uniqueness of the substring sequences within the reference genome relative to the number of cells and operations needed to identify groups of cells or columns storing matching sequences.

Example Processes

Figure 3:
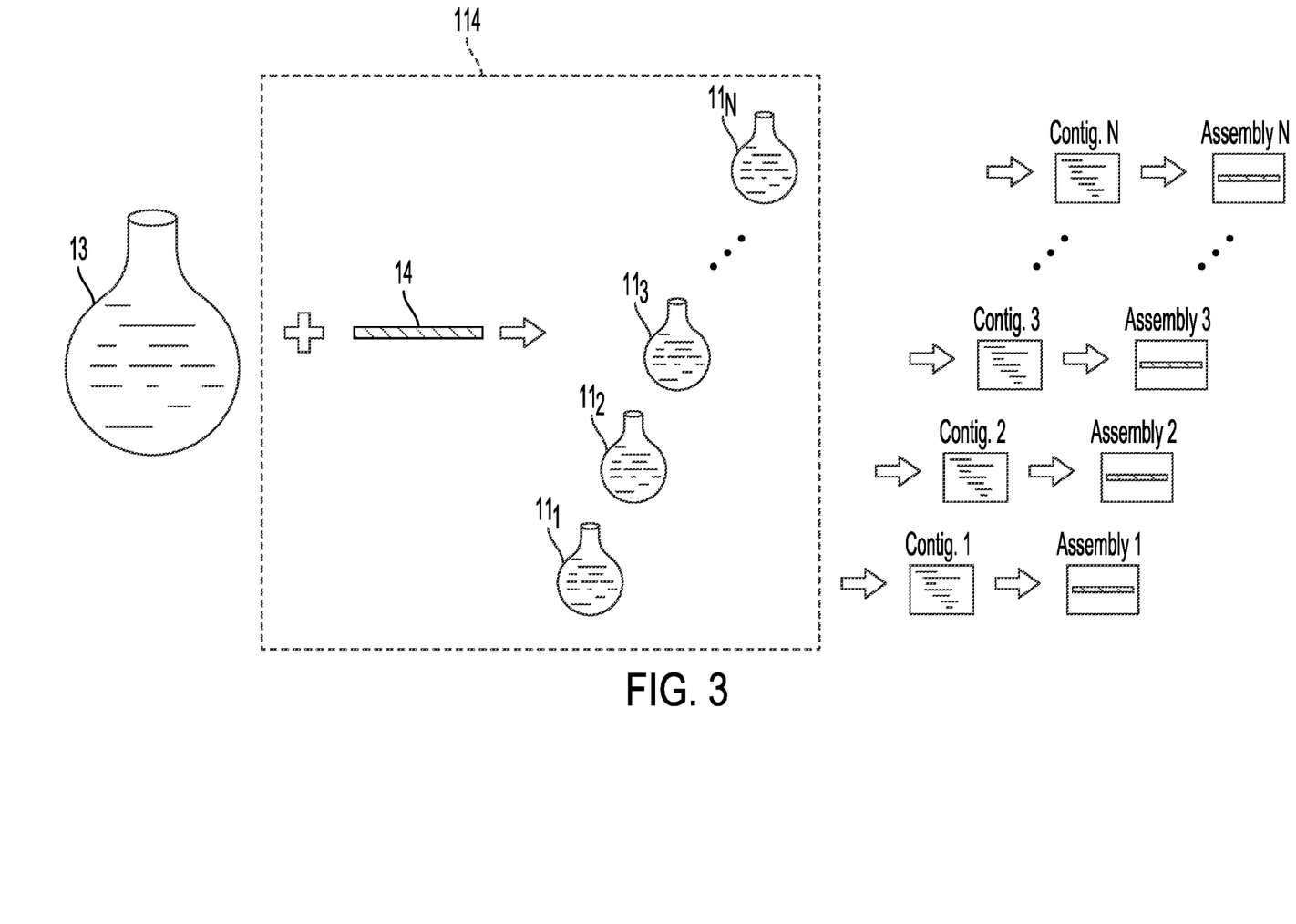
FIG. 3 illustrates an example of de novo genome sequencing according to one or more embodiments.

FIG. 3 illustrates an example of de novo sequencing according to one or more embodiments. As shown in FIG. 3, a plurality of sample reads 13 are compared to reference genome 14 using reference-guided device 102 to sort the plurality of reads into smaller sample groups 11$_1$ to 11$_N$ in a pre-processing 114. Each sample group 11 includes sample reads from the plurality of sample reads 13 that correspond to a portion of reference genome 14, such as H38, based on probabilistic locations of the sample reads within reference genome 14. Sample reads in each group can then be aligned with other sample reads in the same sample group 11 to form contigs 1 to N or overlapping DNA segments, which correspond to sample groups 11$_1$ to 11$_N$. The alignment of the sample reads may be performed by comparing the sample reads to other sample reads in the same sample group 11 using one or more algorithms, such as seed and extend algorithms known in the art for performing de novo sequencing. Each contig is then assembled to form corresponding assemblies 1 to N, which may then be mapped to chromosomes to complete the sequencing of the genome.

The portions of the de novo sequencing shown outside of pre-processing 114 may be performed by hosts 101 independently, which improves the scalability and efficiency of de novo sequencing, as compared to conventional de novo sequencing where all the sample reads may be stored in a single shared memory. In the example of FIG. 3, the sorting of the plurality of sample reads 13 into sample groups 11 allows for the sample reads to be stored in a number of N memories, such as DRAM, that are smaller than using a single memory to store all of the sample reads, as in conventional de novo sequencing. As noted above, the number of compute cores that can connect to a larger shared memory, such as a 2 TB DRAM, with independent high-bandwidth channels is limited (e.g., up to 24 cores), which limits the number of independent compute threads (e.g., up to 128 compute threads) that can be used for assembling and mapping the sample reads into a sequenced genome.

The arrangement shown in FIG. 3, on the other hand, can improve scalability so that each smaller memory storing a respective sample group can be accessed by a maximum number of independent high-bandwidth channels, resulting in a greater total number of processing cores and independent compute threads, as compared to a conventional arrangement where the plurality of sample reads are stored in a single shared memory. In addition, the efficiency of assembling and mapping the sample reads is increased by probabilistically localizing the sample reads. The sample reads may also be nearly evenly divided among the sample groups, such as within 10% of each other, to distribute the workload among hosts 101 and improve parallelization.

For example, if the plurality of reads 13 includes X=200, 000 long reads (e.g., reads from a nanopore device resulting in 5,000 bases per sample read), each sample group 11 may include 200 sample reads with N=1,000 sample groups 11. The size required to store the sample reads in each shared memory for a sample group 11 is then reduced by a factor of N, resulting in a reduction in overall cost for 1,000 smaller memories as compared to a single large memory. Each sample group 11 may then be accessed by Y=24 processing cores. The resulting parallelization can increase the overall number of cores that can be used for assembling the sample reads from 24 in the conventional example of a single shared memory to 24,000 cores in the example of 1,000 memories storing respective sample groups 11.

Figure 4:
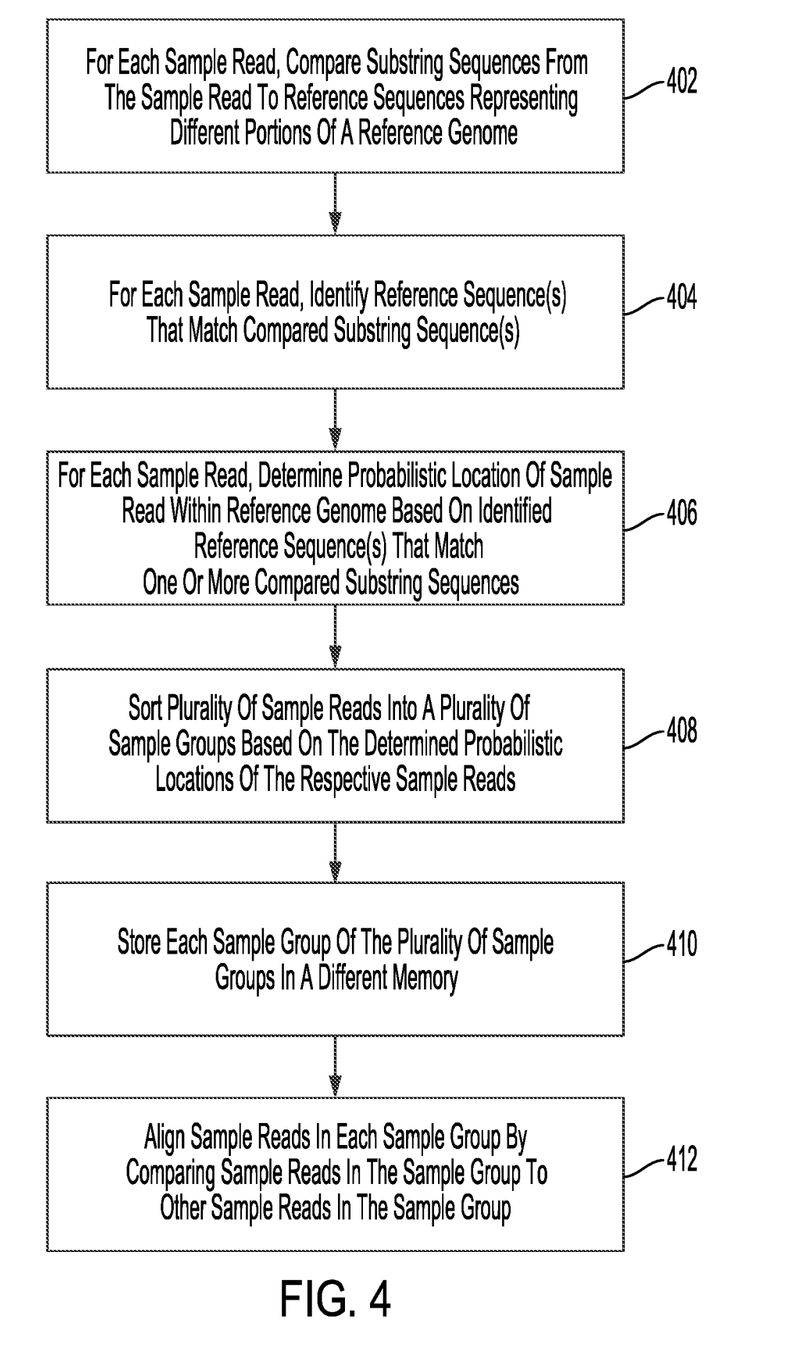
FIG. 4 is a flowchart for a de novo genome sequencing process according to one or more embodiments.

FIG. 4 is a flowchart for a de novo genome sequencing process according to one or more embodiments. The process of FIG. 4 can be performed by, for example, system 100 including reference-guided device 102 and hosts 101.

In block 402, for each sample read of a plurality of sample reads (e.g., the plurality of sample reads 13 in FIG. 3), substring sequences from the sample read are compared to reference sequences representing different portions of a reference genome (e.g., reference genome 14 in FIG. 3). In some implementations, the comparison can include determining a comparison value for each group of cells in a plurality of groups of cells (e.g., array(s) 104 in FIG. 1) representing a result of the comparison of a substring sequence stored in the group of cells to a reference sequence stored in the group of cells.

The substring sequences include a contiguous sequence of bases from the sample read. The substring sequences may be randomly chosen by one or more hosts 101 or by device 102. In other implementations, the substring sequences may be selected so that the substring sequences are spread throughout the sample read. As discussed in related co-pending application Ser. No. 16/820,711, substring sequences with lengths between 17 and 25 bases can provide a sufficient number of unique matches for most substring sequences (i.e., only matching at one location within a reference genome) for locating the substring sequence within a reference genome, such as H38. A substring length shorter than 17 bases will require a greater number of substring sequences from a sample read to determine the probabilistic location of the sample read within the reference genome. In the case of reference genome H38, a substring length shorter than 15 bases, may fail to identify any unique matches within the reference genome for nearly all the substring sequences attempted.

On the other hand, a substring length greater than 25 bases, incurs additional storage cost in terms of cells in array(s) 104 in device 102 and a greater computational cost due to the increase in operations needed to find matching sequences, with little improvement in the number of unique matches. As a result, the example of FIG. 2 discussed above uses a substring length of 20 bases, which means that each group of cells 110 in FIG. 2 includes a predetermined number of 20 cells. Those of ordinary skill in the art will appreciate with reference to the present disclosure that a different substring length or a different predetermined number of cells in each group of cells in device 102 may be preferred for other examples, such as when using a different reference genome or a portion of reference genome, as may be the case for medical diagnosis or genetic screening for a condition related to a particular portion of a reference genome. In addition, different tradeoffs between computational cost, the number of cells, and accuracy in terms of a greater number of unique matches may also affect the number of cells used for each group of cells in array(s) 104.

In block 404, one or more reference sequences are identified for each sample read that match one or more compared substring sequences from the sample read. In identifying matching reference sequences, groups of cells 110 in array(s) 104 of device 102 may be identified as storing a reference sequence representing a portion of the reference genome, as discussed above with the example of array 104 in FIG. 2. In some implementations, the identification may be made by device 102 using logic gates, such as, for example, by a combination of XNOR and AND gates of cells in array(s) 104 and/or circuitry 106 of device 102. In other implementations, the identification of matching reference sequences or groups of cells storing matching reference sequences may be made by performing calculations using the stored reference values and sample values for the bases, such as by using an inner-product or a dot product of the values. Examples of identifying reference sequences that match a substring sequence loaded or stored in array(s) 104 are provided in related co-pending application Ser. No. 16/820,711.

In block 406, system 100 determines for each sample read a probabilistic location of the sample read within the reference genome based on the one or more identified reference sequences that match the one or more compared substring sequences. In this regard, a first matching group of cells in array(s) 104 of device 102 may be used as a location for each substring sequence, or alternatively, multiple matching groups of cells may be used as possible locations for the substring sequence, assuming some substring sequences result in multiple matching groups of cells. In some cases, there may be no matching locations for a substring sequence due to errors in the substring sequence, such as read errors caused by a read device or mutations in the sample read. The location for the sample read determined in block 406 by circuitry 106 or a host 101 can be probabilistic in the sense that multiple possible locations can be identified for different substring sequences from the sample read, and a consensus or statistic derived from the matching locations can be used to probabilistically locate the sample read within the reference genome.

In one example, a mean of all the locations of all of the matching groups of cells for all the substring sequences is used to identify a most likely location of the sample read within the reference genome. In another example, only one location for each substring sequence with a matching group of cells is used in the mean. In yet another example, a probabilistic location of the sample read may be determined by identifying the farthest apart locations within the reference genome that correspond to matching groups of cells for the substring sequences. In other examples, one or more outlier locations with respect to a group of matching locations may be discarded in determining the probabilistic location of the sample read within the reference genome.

In block 408, device 102 or one or more of hosts 101 sort the plurality of sample reads into a plurality of sample groups based on the determined probabilistic locations of the respective sample reads. Each sample group may include approximately the same number of sample reads (e.g., within 10% of each other) to more evenly distribute the workload of assembling and mapping the sample reads among the hosts 101. In some implementations, index 10 or a portion of a data structure may be provided by device 102 to hosts 101 indicating a group of sample reads to be processed by the host 101 as a sample group 11. In such implementations, each host 101 may then retrieve the sample reads corresponding to the assigned sample group 11 from a shared memory. In other implementations, device 102 may provide each host 101 with sample reads that have been probabilistically located within a sample group 11 assigned to the host. In yet other implementations, the sample reads for an assigned sample group may be retrieved from another host 101.

In block 410, each sample group 11 is stored in a different memory. In some implementations, each host 101 may include its own memory, such as memory 112 for storing its assigned sample group 11. As discussed above, using a large number of memories distributed among hosts 101 is ordinarily less expensive than storing all of the plurality of sample reads in a single large memory, such as a 2 TB DRAM. Moreover, each memory can be accessed locally by a processor 109 of the host 101 and allow for a greater number of compute threads to operate simultaneously in parallel throughout system 100. This can provide for a faster sequencing or assembly of the sample reads.

In block 412, the sample reads in each sample group are aligned by comparing the sample reads in the sample group to other sample reads in the sample group. The comparisons in block 412 can be completed quicker than randomly comparing sample reads from one large plurality of sample reads, as in conventional de novo sequencing, because there are less sample reads in each localized sample group and a greater probability of overlapping sample reads due to the pre-processing performed in blocks 402 to 408 discussed above.

As will be appreciated by those of ordinary skill in the art with reference to the present disclosure, the order of the blocks shown in FIG. 4 may differ in other implementations. For example, blocks 402 to 406 may be repeated in sequence for iterations of sample reads before proceeding to sorting the plurality of sample reads in block 408.

Even though the genome sequencing of FIG. 4 is de novo, as opposed to reference-aligned sequencing, the process of FIG. 4 uses a novel technique of reference-guided genome sequencing to pre-process or sort the sample reads into groups of probabilistically localized sample reads to improve the efficiency, cost, and scalability of de novo sequencing. The example processes discussed below for reference-aligned sequencing also pre-process or sort a plurality of sample reads into groups of probabilistically localized sample reads to improve the efficiency, cost, and scalability of reference-aligned sequencing. In addition, the reference-aligned sequencing examples discussed with reference to FIGS. 5 and 6 below further provide for partitioning the reference genome for reference-aligned sequencing.

Figure 5:
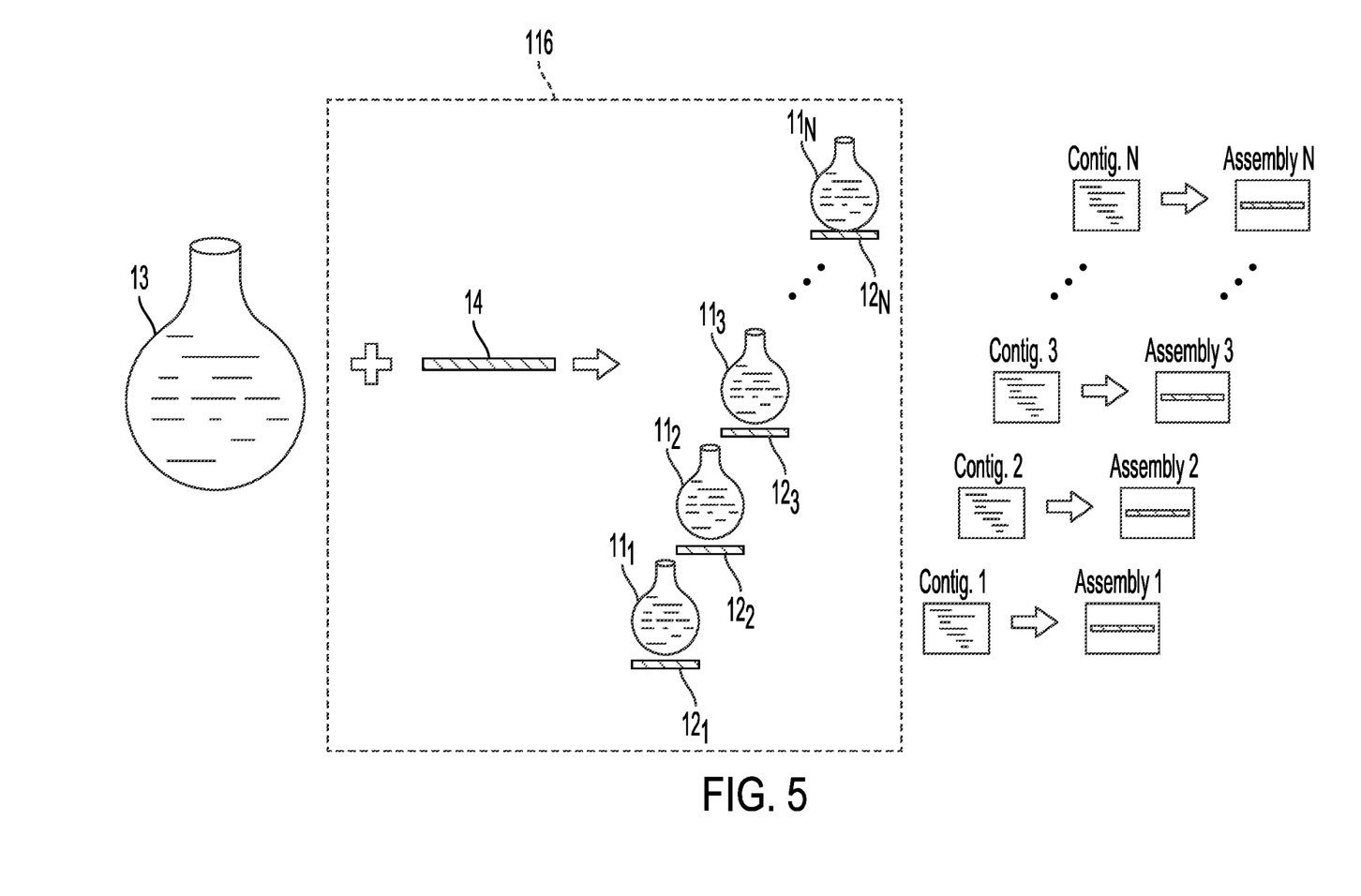
FIG. 5 illustrates an example of reference-aligned genome sequencing according to one or more embodiments.

FIG. 5 illustrates an example of reference-aligned genome sequencing according to one or more embodiments. As shown in FIG. 5, and similar to the example of de novo sequencing in FIG. 3 discussed above, a plurality of sample reads 13 are compared to reference genome 14 using reference-guided device 102 to sort the plurality of sample reads into smaller sample groups $11_1$ to $11_N$ in pre-processing 116. However, unlike the example of de novo sequencing in FIG. 3, the reference-aligned sequencing of FIG. 5 further includes partitioning reference genome 14 into reference partitions $12_1$ to $12_N$ that are associated with the probabilistic locations determined for respective sample groups $11_1$ to $11_N$ in pre-processing 116. In some implementations, each reference partition 12 may be stored in the same memory (e.g., memory 112 in FIG. 1) as the associated sample group 11. In other implementations, the sample group 11 and the associated reference partition 12 may be stored in different memories.

By storing each of reference partitions $12_1$ to $12_N$ in different memories in FIG. 5, less memory is needed as would be needed to store the entire reference genome 14 at each host 101 for randomly grouped sample reads without knowing which parts of the reference genome included the randomly grouped sample reads. The partitioning of reference genome 14 into smaller reference partitions 12 is made possible by pre-processing 116 to sort sample reads 13 into probabilistically localized sample groups $11_1$ to $11_N$, thereby associating portions of the reference genome with particular sample groups 11.

In some implementations, portions of the reference genome may be discarded or not used in any of reference partitions $12_1$ to $12_N$ if there are no sample reads having probabilistic locations within that portion of the reference genome. Such cases may result from, for example, medical diagnostics or genetic screening that may only relate to particular portions of a reference genome. In such cases, the efficiency of reference-aligned sequencing in terms of processing resources, memory resources, and time is further improved by not having to store and make comparisons to the full reference genome.

In the example of FIG. 5, each sample group 11 includes approximately the same number of sample reads from the plurality of sample reads 13 (e.g., within 10% of each other) that correspond to a reference partition 12 of reference genome 14, such as H38, based on probabilistic locations of the sample reads within reference genome 14. Sample reads in each sample group 11 are then aligned with other sample reads in the same sample group 11 to form contigs 1 to N or overlapping DNA segments, which correspond to sample groups $11_1$ to $11_N$. The alignment of the sample reads can be performed by comparing the sample reads in the sample group 11 to the localized reference partition 12 using one or more algorithms, such as seed and extend algorithms known in the art for performing reference-aligned sequencing. Each contig is then assembled to form corresponding assemblies 1 to N, which may then be mapped to chromosomes to complete the sequencing of the sample genome.

In addition, the use of multiple memories to store portions of the reference genome for reference-aligned sequencing improves the scalability and efficiency of reference-aligned sequencing, as compared to a conventional reference-aligned sequencing where the entire reference genome may be stored in a single shared memory, such as in a 16 GB DRAM. As noted above, the number of compute cores that can connect to a such a shared memory with independent high-bandwidth channels is limited (e.g., up to 24 cores), which limits the number of independent compute threads (e.g., up to 128 compute threads) that can be used for assembling and mapping the sample reads into a sequenced genome.

The arrangement shown in FIG. 5, on the other hand, can improve scalability so that each smaller memory storing a respective reference partition 12 can be accessed by a maximum number of independent high-bandwidth channels, resulting in a greater total number of processing cores and independent compute threads, as compared to a conventional arrangement where the entire reference genome may be stored in a single shared memory. In addition, the efficiency of assembling and mapping the sample reads is increased by probabilistically localizing the sample reads.

Figure 6:
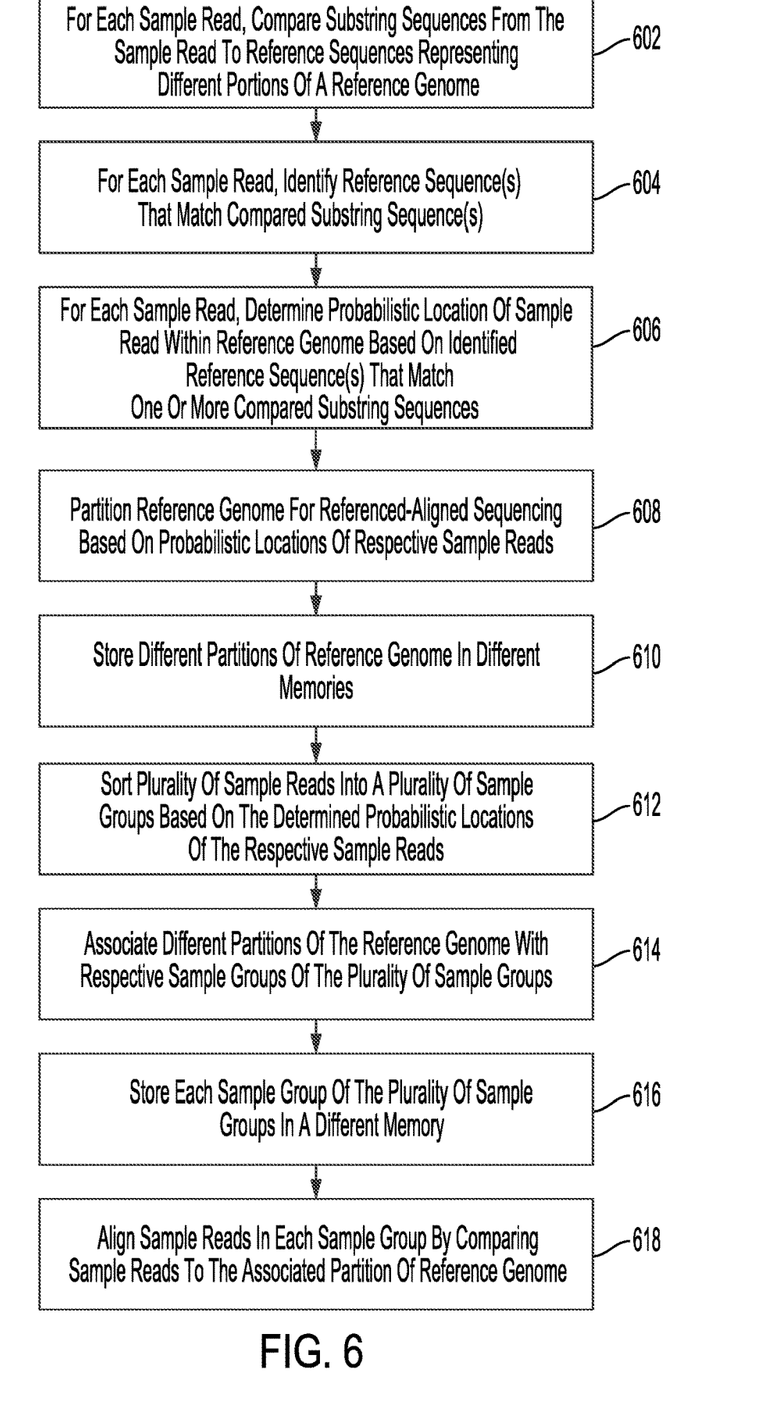
FIG. 6 is a flowchart for a reference-aligned genome sequencing process according to one or more embodiments.

FIG. 6 is a flowchart for a reference-aligned genome sequencing process according to one or more embodiments. The process of FIG. 4 can be performed by, for example, system 100 including reference-guided device 102 and hosts 101.

In block 602, for each sample read of a plurality of sample reads (e.g., the plurality of sample reads 13 in FIG. 3), substring sequences from the sample read are compared to reference sequences representing different portions of a reference genome (e.g., reference genome 14 in FIG. 5). The substring sequences include a contiguous sequence of bases from the sample read. The substring sequences may be randomly chosen by one or more hosts 101 or by device 102. In other implementations, the substring sequences may be selected so that the substring sequences are spread throughout the sample read. As discussed in related co-pending application Ser. No. 16/820,711, and as noted above, substring sequences with lengths between 17 and 25 bases can provide a sufficient number of unique matches for most substring sequences (i.e., only matching at one location within a reference genome) for locating the substring sequence within a reference genome, such as H38.

Those of ordinary skill in the art will appreciate with reference to the present disclosure that a different substring length or a different predetermined number of cells in each group of cells in device 102 may be preferred for other examples, such as when using a different reference genome or a portion of reference genome, as may be the case for medical diagnosis or screening for a genetic condition related to a particular portion of a reference genome. In addition, different tradeoffs between computational cost, the number of cells in array(s) 104 of device 102, and accuracy in terms of a greater number of unique matches may also affect the number of cells used for each group of cells in array(s) 104.

In block 604, for each sample read, one or more reference sequences are identified that match one or more of the compared substring sequences taken from the sample read. In identifying matching reference sequences, groups of cells 110 in array(s) 104 of device 102 may be identified as storing a reference sequence representing a portion of the reference genome, as discussed above with the example of array 104 in FIG. 2. In some implementations, the identification may be made by device 102 using logic gates, such as, for example, by a combination of XNOR and AND gates of cells in array(s) 104 and/or circuitry 106 of device 102. In other implementations, the identification of matching reference sequences or groups of cells storing matching reference sequences may be made by performing calculations using the stored reference values and sample values for the bases, such as by using an inner-product or a dot product of the values.

In block 606, system 100 determines a probabilistic location for each sample read within the reference genome based on the one or more reference sequences that match one or more compared substring sequences. A first matching group of cells in array(s) 104 of device 102 may be used as a location for each substring sequence, or alternatively, multiple matching groups of cells may be used as possible locations for the substring sequence, assuming some substring sequences result in multiple matching groups of cells. In some cases, a substring sequence may not have any matching reference sequences. The location for the sample read determined in block 606 by circuitry 106 of device 102 or a host 101 can be probabilistic in the sense that multiple possible locations can be identified for different substring sequences from the sample read, and a consensus or statistic derived from the matching locations can be used to probabilistically locate the sample read within the reference genome.

In one example, a mean of all the locations of all of the matching groups of cells for all the substring sequences is used to identify a most likely location of the sample read within the reference genome. In another example, only one location for each substring sequence with a matching group of cells is used in the mean. In yet another example, a probabilistic location of the sample read may be determined by identifying the farthest apart locations within the reference genome that correspond to matching groups of cells for the substring sequences. In other examples, one or more outlier locations with respect to a group of matching locations may be discarded in determining the probabilistic location of the sample read within the reference genome.

In block 608, device 102 or one or more of hosts 101 partition the reference genome for reference-aligned sequencing based on the probabilistic locations determined in block 606 for respective sample reads. The partitions of the reference genome may vary in size based on a distribution of the locations determined for the sample reads. For example, the size of the partitions may be based on the number of sample reads located in the partition such that each partition is associated with a sample group having an approximately equal number of sample reads, such as by each reference partition or sample group having within 10% of the number of sample reads as the other reference partitions or sample groups. In other implementations, the partitions of the reference genome may be equally divided, and a larger variation in the number of sample reads among the sample groups may be allowed.

In this regard, some portions of the reference genome may be discarded or not assigned to a sample group if there are no sample reads having probabilistic locations within that portion of the reference genome. Such cases may result from, for example, medical diagnostics or screening that may only relate to particular portions of a reference genome. In such cases, the efficiency of reference-aligned sequencing in terms of processing resources, memory resources, and time is further improved by not having to store and make comparisons to the full reference genome.

In block 610, the different partitions of the reference genome are stored in different memories, such as in memories 112 of hosts 101. Each host 101 may receive a portion of the reference genome from device 102 or from another device, such as a shared memory in system 100 storing the reference genome. As discussed above with reference to FIG. 5, storing localized partitions of the reference genome in different memories can allow for parallel processing by a greater number of processing cores without having to store the entire reference genome in multiple larger memories, as would be the case if the sample reads were randomly grouped.

In block 612, device 102 or one or more of hosts 101 sort the plurality of sample reads into a plurality of sample groups based on the determined probabilistic locations of the respective sample reads. The sample reads may be sorted so that each sample group includes approximately the same number of sample reads (e.g., within a range of 10% of the sample group having the most sample reads). In some implementations, index 10 or a portion of a data structure may be provided by device 102 to hosts 101 indicating a group of sample reads to be processed by the host 101 as a sample group 11. In such implementations, each host 101 may then retrieve the sample reads corresponding to the assigned sample group 11 from a shared memory. In other implementations, device 102 may provide each host 101 with sample reads that have been probabilistically located within a sample group 11 assigned to the host 101. In yet other implementations, the sample reads for an assigned sample group may be retrieved from another host 101.

In block 614, different partitions of the reference genome are associated with respective sample groups based on the probabilistic locations of the sample reads in the sample group. As noted above, the partitions of the reference genome may vary in size based on the distribution of the probabilistic locations determined for the sample reads within the sample group. In this regard, the size of the partitions may be based on the number of sample reads located in the partition such that each partition is associated with an approximately equal number of sample reads. In other implementations, the partitions of the reference genome may be equally divided without considering the distribution of the sample reads within the sample group.

In block 616, each sample group 11 is stored in a different memory, which may be the same or a different memory used to store the associated partition of the reference genome in block 610. In some implementations, each host 101 may include its own memory, as with memories 112 in FIG. 1 storing respective, associated sample groups 11 and reference genome partitions 12. As discussed above, using a greater number of memories distributed among hosts 101 is ordinarily less expensive than storing all of the plurality of sample reads in a single large memory, such as a 2 TB DRAM. Moreover, each memory can be accessed by a processor 109 of the host 101 and allow for a greater number of compute threads to operate simultaneously in parallel. This can provide for a faster sequencing or assembly of the sample reads.

In block 618, the sample reads in each sample group are aligned by comparing the sample reads in the sample group to the associated partition of the reference genome for the sample group. The comparisons in block 618 can be completed quicker than comparing sample reads to the full reference genome as in conventional techniques of reference-aligned sequencing, because there are less comparisons needed to locate the sample reads in the sample group due to the smaller size of the partition of the reference genome. In addition, the storage of a smaller partition of the reference genome in more memories facilitates greater scalability to allow for more compute threads to access the partitions of the reference genome stored in the different memories.

As will be appreciated by those of ordinary skill in the art with reference to the present disclosure, the order of the blocks shown in FIG. 6 may differ in other implementations.

For example, the partitioning of the reference genome in block 608 may occur after sorting the plurality of sample reads into a plurality of sample groups in block 612. As another example, each sample group may be stored in a different memory in block 616 before storing the different partitions of the reference genome in different memories in block 610. As yet another example, blocks 602 to 606 may be repeated in sequence for iterations of sample reads before proceeding to partitioning the reference genome in block 408.

As discussed above, the foregoing reference-guided devices and methods ordinarily allow sample reads to be probabilistically located within a reference genome. This can improve the efficiency of de novo and reference-aligned sequencing by pre-processing sample reads into groups based on their locations in the reference genome for further sequencing. In the case of de novo sequencing, this can improve the scalability and efficiency of de novo sequencing by allowing more compute threads to access multiple localized groups of sample reads in smaller memories, as compared to conventional methods where a larger and more expensive memory is used to access all of the sample reads by a smaller number of compute threads. In the case of reference-aligned sequencing, the localized groups of sample reads allow for a smaller and statistically more relevant portion of a reference genome to be stored in a smaller and less expensive memory for each localized group, while also allowing for more compute threads to access the multiple smaller memories to improve scalability, as compared to a conventional reference-aligned sequencing that may use one or significantly fewer shared memories that each store the full reference genome.

Other Embodiments

Those of ordinary skill in the art will appreciate that the various illustrative logical blocks, modules, and processes described in connection with the examples disclosed herein may be implemented as electronic hardware, software, or combinations of both. Furthermore, the foregoing processes can be embodied on a computer readable medium which causes a processor, controller, or other circuitry to perform or execute certain functions.

To clearly illustrate this interchangeability of hardware and software, various illustrative components, blocks, and modules have been described above generally in terms of their functionality. Whether such functionality is implemented as hardware or software depends upon the particular application and design constraints imposed on the overall system. Those of ordinary skill in the art may implement the described functionality in varying ways for each particular application, but such implementation decisions should not be interpreted as causing a departure from the scope of the present disclosure.

The various illustrative logical blocks, units, modules, and circuitry described in connection with the examples disclosed herein may be implemented or performed with a general purpose processor, a GPU, a DSP, an ASIC, an FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. Processor or controller circuitry may also be implemented as a combination of computing devices, e.g., a combination of a DSP and a microprocessor, a plurality of microprocessors, an SoC, one or more microprocessors in conjunction with a DSP core, or any other such configuration.

The activities of a method or process described in connection with the examples disclosed herein may be embodied directly in hardware, in a software module executed by processor or controller circuitry, or in a combination of the two. The steps of the method or algorithm may also be performed in an alternate order from those provided in the examples. A software module may reside in RAM memory, flash memory, ROM memory, EPROM memory, EEPROM memory, registers, hard disk, a removable media, an optical media, or any other form of storage medium known in the art. An exemplary storage medium is coupled to processor or controller circuitry such that the processor or controller circuitry can read information from, and write information to, the storage medium. In the alternative, the storage medium may be integral to processor or controller circuitry. The processor or controller circuitry and the storage medium may reside in an ASIC or an SoC.

The foregoing description of the disclosed example embodiments is provided to enable any person of ordinary skill in the art to make or use the embodiments in the present disclosure. Various modifications to these examples will be readily apparent to those of ordinary skill in the art, and the principles disclosed herein may be applied to other examples without departing from the spirit or scope of the present disclosure. The described embodiments are to be considered in all respects only as illustrative and not restrictive. In addition, the use of language in the form of "at least one of A and B" in the following claims should be understood to mean "only A, only B, or both A and B."

What is claimed is:

1. A method of processing a plurality of sample reads for genome sequencing using at least one systolic array including a plurality of groups of cells, the method comprising:
   for each sample read of the plurality of sample reads:
      comparing substring sequences from the sample read to reference sequences representing different portions of a reference genome by storing the substring sequences in the plurality of groups of cells of the at least one systolic array, wherein each group of the plurality of groups of cells further stores a reference sequence for comparison to the sub string sequences;
      identifying one or more stored reference sequences that match one or more of the compared substrings; and
      determining a probabilistic location of the sample read within the reference genome based on the one or more identified reference sequences; and
   partitioning the reference genome for referenced-aligned genome sequencing based at least in part on the determined probabilistic locations of the plurality of sample reads.

2. The method of claim 1, further comprising storing different partitions of the reference genome in different memories.

3. The method of claim 1, further comprising sorting the plurality of sample reads into a plurality of sample groups based on the determined probabilistic locations of the plurality of sample reads.

4. The method of claim 3, further comprising storing each sample group of the plurality of sample groups in a different memory.

5. The method of claim 3, further comprising:
   associating different partitions of the reference genome with respective sample groups of the plurality of sample groups; and aligning sample reads in each sample group of the plurality of sample groups by comparing the sample reads to the associated partition of the reference genome.

6. The method of claim 5, further comprising using different processors to align sample reads in respective sample groups of the plurality of sample groups.

7. The method of claim 1, wherein partitioning the reference genome based at least in part on the determined probabilistic locations of the plurality of sample reads precedes the performance of at least one of an exact matching algorithm and an approximate matching algorithm for genome sequencing.

8. The method of claim 1, further comprising partitioning the reference genome such that at least two different partitions of the reference genome have different sizes based on a distribution of probabilistic locations determined for sample reads of the plurality of sample reads.

9. A method of operating a system for processing a plurality of sample reads for genome sequencing, the method comprising:
for each sample read of the plurality of sample reads:
comparing substring sequences from the sample read to reference sequences representing different portions of a reference genome, the comparing comprising:
storing the sub string sequences in a plurality of groups of cells of the system one substring at a time, wherein each group of cells of the plurality of groups of cells further stores a reference sequence that partially overlaps another reference sequence stored in at least one other group of cells of the plurality of groups of cells; and
identifying one or more groups of cells of the plurality of groups of cells where the stored reference sequence matches the sub string sequence stored in the groups of cells, wherein each cell of the plurality of groups of cells includes logic circuitry for comparing a sample value of the stored substring sequence to a reference value of the stored reference sequence; and
determining a probabilistic location of the sample read within the reference genome based on the one or more identified groups of cells; and
partitioning the reference genome for referenced-aligned genome sequencing based at least in part on the determined probabilistic locations of the plurality of sample reads.

10. The method of claim 9, further comprising storing different partitions of the reference genome in different memories of the system.

11. The method of claim 10, further comprising sorting the plurality of sample reads into a plurality of sample groups based on the determined probabilistic locations of the plurality of sample reads.

12. The method of claim 11, further comprising storing each sample group of the plurality of sample groups in a different memory of the system.

13. The method of claim 11, further comprising:
associating different partitions of the reference genome with respective sample groups of the plurality of sample groups; and
aligning sample reads in each sample group of the plurality of sample groups by comparing the sample reads to the associated partition of the reference genome.

14. The method of claim 13, further comprising using different processors of the system to align sample reads in respective sample groups of the plurality of sample groups.

15. The method of claim 9, wherein partitioning the reference genome based at least in part on the determined probabilistic locations of the plurality of sample reads precedes the performance of at least one of an exact matching algorithm and an approximate matching algorithm for genome sequencing.

16. A system for processing a plurality of sample reads for genome sequencing, the system comprising:
at least one systolic array including a plurality of groups of cells;
circuitry configured to:
for each sample read of the plurality of sample reads:
store substring sequences from the sample read in the plurality of groups of cells one sub string sequence at a time for comparison to reference sequences representing different portions of a reference genome, wherein each group of cells of the plurality of groups of cells further stores a reference sequence that partially overlaps another reference sequence stored in at least one other group of cells of the plurality of groups of cells;
identify one or more groups of cells of the plurality of groups of cells where the stored reference sequence matches the sub string sequence stored in the group of cells; and
determine a probabilistic location of the sample read within the reference genome based at least in part on the one or more identified groups of cells; and
at least one processor configured to partition the reference genome for referenced-aligned genome sequencing based at least in part on the determined probabilistic locations for the plurality of sample reads.

17. The system of claim 16, further comprising a plurality of memories configured to store different partitions of the reference genome in different memories of the plurality of memories.

18. The system of claim 16, wherein the at least one processor is further configured to sort the plurality of sample reads into a plurality of sample groups based on the determined probabilistic locations of the plurality of sample reads.

19. The system of claim 18, further comprising a plurality of memories each configured to store a respective sample group of the plurality of sample groups.

20. The system of claim 18, wherein the at least one processor is further configured to:
associate different partitions of the reference genome with respective sample groups of the plurality of sample groups; and
align sample reads in each sample group of the plurality of sample groups by comparing the sample reads to the associated partition of the reference genome.

21. The system of claim 20, wherein different processors of the at least one processor align sample reads in respective sample groups of the plurality of sample groups.

* * * * *